United States Patent
Horiuchi

(10) Patent No.: US 9,652,837 B2
(45) Date of Patent: May 16, 2017

(54) METHOD OF DETERMINING QUALITY OF HEART AND CUPID OPTICAL EFFECTS OF DIAMOND DEVICE THEREFOR

(75) Inventor: Nobuo Horiuchi, Tokyo (JP)

(73) Assignee: CENTRAL GEM LABORATORY, Tokyo (JP)

( * ) Notice: Subject to any disclaimer, the term of this patent is extended or adjusted under 35 U.S.C. 154(b) by 215 days.

(21) Appl. No.: 14/411,513

(22) PCT Filed: Jun. 29, 2012

(86) PCT No.: PCT/JP2012/066709
§ 371 (c)(1),
(2), (4) Date: Dec. 28, 2014

(87) PCT Pub. No.: WO2014/002254
PCT Pub. Date: Jan. 3, 2014

(65) Prior Publication Data
US 2015/0187065 A1    Jul. 2, 2015

(51) Int. Cl.
*G01N 21/87* (2006.01)
*G06T 7/00* (2017.01)

(52) U.S. Cl.
CPC .......... *G06T 7/0004* (2013.01); *G01N 21/87* (2013.01); *G06T 7/0006* (2013.01); *G06T 2207/30108* (2013.01)

(58) Field of Classification Search
None
See application file for complete search history.

(56) References Cited

U.S. PATENT DOCUMENTS

| 7,414,709 B2 * | 8/2008 | Wagner | G01N 21/87 356/30 |
| 8,239,211 B2 * | 8/2012 | Feldman | G01N 21/87 705/1.1 |

(Continued)

FOREIGN PATENT DOCUMENTS

| JP | 6-160287 A | * | 6/1994 | ............. G01N 21/87 |
| JP | 06-160287 A | | 6/1994 | |

(Continued)

OTHER PUBLICATIONS

English Translation of JP 2003-194725A, Overseas Diamonds, Jul. 9, 2003.*

(Continued)

*Primary Examiner* — Sath V Perungavoor
*Assistant Examiner* — Janese Duley
(74) *Attorney, Agent, or Firm* — Hedman & Costigan, P.C.; James V. Costigan; Kathleen A. Costigan

(57) ABSTRACT

The present invention includes the steps of: storing data such as the symmetry, the variation degree in the area, the displacement of a tip portion, the depth of a slit, the shoulder widths, and the like of eight heart marks and the symmetry, the variation degree in the area, the displacement or sharpness of an arrow tip, and the like of eight cupid marks into a computer database; and performing arithmetic processing of the data and ranking determination of the quality of the heart marks and the cupid marks. It is an object of the present invention to provide a method and device capable of objectively determining the quality on the basis of the same determination criterion using determination software in both of a case where the diamond is directly imaged by a CCD camera.

2 Claims, 18 Drawing Sheets

(56) References Cited

U.S. PATENT DOCUMENTS

2005/0187831 A1* 8/2005 Gershburg ......... G06Q 30/0643
705/27.2
2006/0074588 A1* 4/2006 Blodgett .............. A44C 17/001
702/179

FOREIGN PATENT DOCUMENTS

| JP | 07-023273 A | 4/1995 | |
|---|---|---|---|
| JP | 08-271434 A | 10/1996 | |
| JP | 2003-194725 A | * 7/2003 | ............ G01N 21/87 |
| JP | 2008-510972 A | 4/2008 | |

OTHER PUBLICATIONS

English Translation of JP 6-160287 A, Kabushiki Kaisha, Jun. 7, 1994.*

* cited by examiner

FIG. 6 (a)
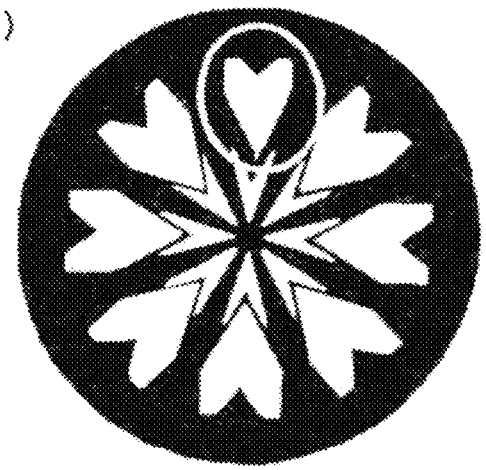
FIG. 6 (b)  FIG. 6 (c)
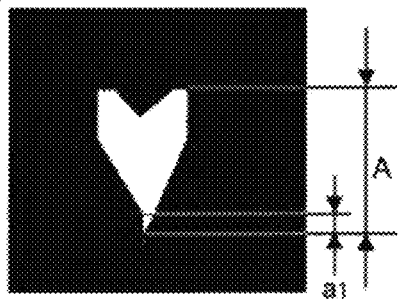 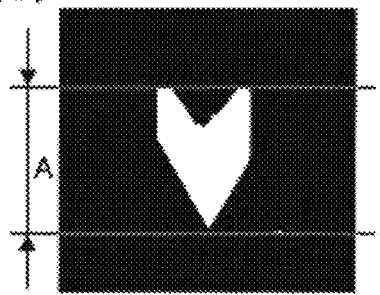
FIG. 6 (d) $A = \dfrac{a_n}{A_n}$  (n=1~8)
FIG. 6 (e)
| DISPLACEMENT OF TIP PORTION OF HEART | NUMBER OF BARS | DETERMINATION |
|---|---|---|
| RANK A | EIGHT PLACES | APPROVAL |
| RANK C | ONE OR MORE PLACES | DISAPPROVAL |
| RANK B | ONE TO THREE PLACES | APPROVAL |
|  | FOUR OR MORE PLACES | DISAPPROVAL |

FIG. 7 (g) $\frac{an}{100}$ (n=1~8)

| DEPTH OF SLIT OF HEART | NUMBER OF BARS | DETERMINATION |
|---|---|---|
| RANK A | EIGHT PLACES | APPROVAL |
| RANK C | ONE OR MORE PLACES | DISAPPROVAL |
| RANK B | ONE TO THREE PLACES | APPROVAL |
|  | FOUR OR MORE PLACES | DISAPPROVAL |

FIG. 8 (a)
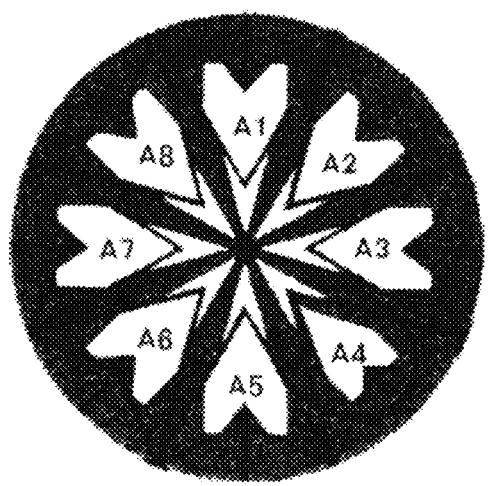
FIG. 8 (b)
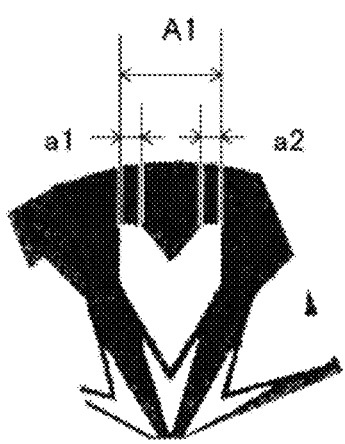
FIG. 8 (c)
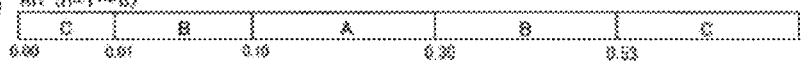
FIG. 8 (d)
| HEART SHOULDER PORTION | NUMBER OF BARS | DETERMINATION |
|---|---|---|
| RANK A | EIGHT PLACES | APPROVAL |
| RANK C | ONE OR MORE PLACES | DISAPPROVAL |
| RANK B | ONE TO THREE PLACES | APPROVAL |
|  | FOUR OR MORE PLACES | DISAPPROVAL |

FIG. 9 (a)
FIG. 9 (b)
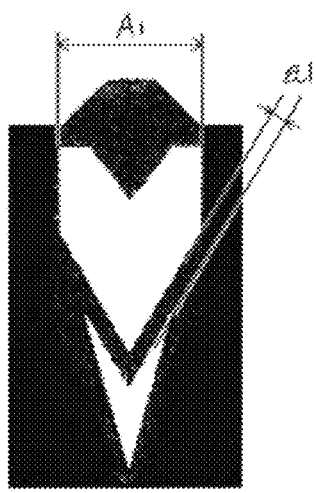
FIG. 9 (c)
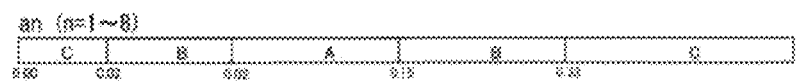
FIG. 9 (d)
| DISTANCE IN BOUNDARY PORTION | NUMBER OF BARS | DETERMINATION |
|---|---|---|
| RANK A | EIGHT PLACES | APPROVAL |
| RANK C | ONE OR MORE PLACES | DISAPPROVAL |
| RANK B | ONE TO THREE PLACES | APPROVAL |
| | FOUR OR MORE PLACES | DISAPPROVAL |

FIG. 10 (a)
FIG. 10 (b)    FIG. 10 (c)
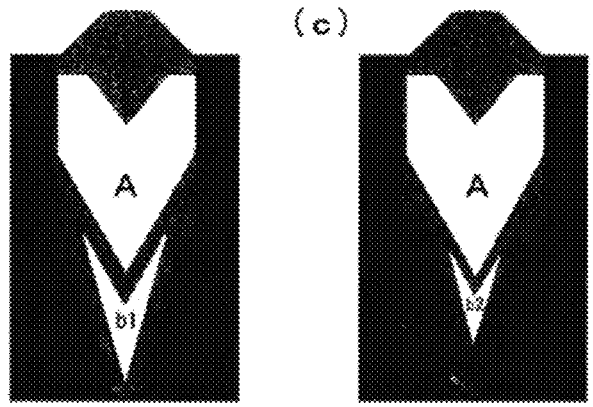
FIG. 10 (d)
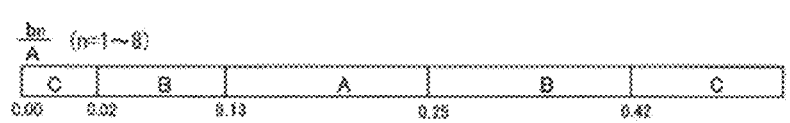
FIG. 10 (e)
| SIZE OF V-SHAPED MARK | NUMBER OF BARS | DETERMINATION |
|---|---|---|
| RANK A | EIGHT PLACES | APPROVAL |
| RANK C | ONE OR MORE PLACES | DISAPPROVAL |
| RANK B | ONE TO THREE PLACES | APPROVAL |
|  | FOUR OR MORE PLACES | DISAPPROVAL |

FIG. 11 (a)
FIG. 11 (b)   FIG. 11 (c)
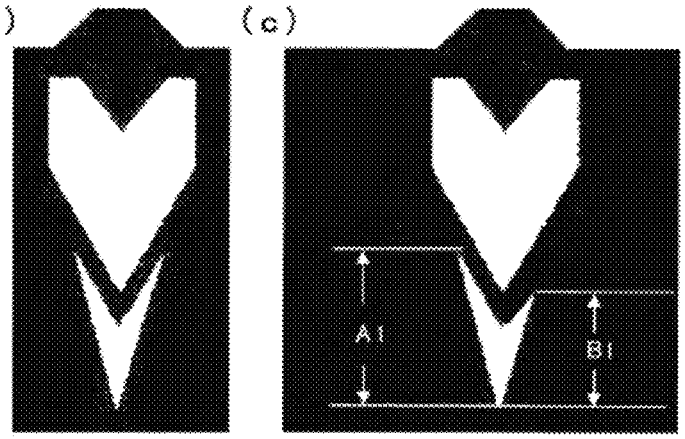
FIG. 11 (d) $\alpha = \frac{Bn}{An}$ (n=1~8)
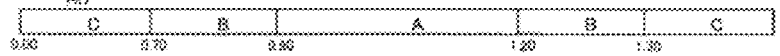
FIG. 11 (e)
| RIGHT AND LEFT LENGTHS OF V-SHAPED MARK | NUMBER OF BARS | DETERMINATION |
|---|---|---|
| RANK A | EIGHT PLACES | APPROVAL |
| RANK C | ONE OR MORE PLACES | DISAPPROVAL |
| RANK B | ONE TO THREE PLACES | APPROVAL |
|  | FOUR OR MORE PLACES | DISAPPROVAL |

(a)

(b) |Σα|

(c) Bmax − Bmin (a)

FIG. 14 (a)
FIG. 14 (b)
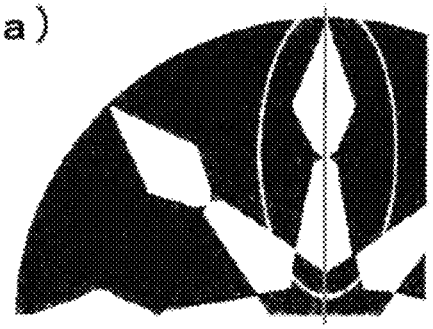
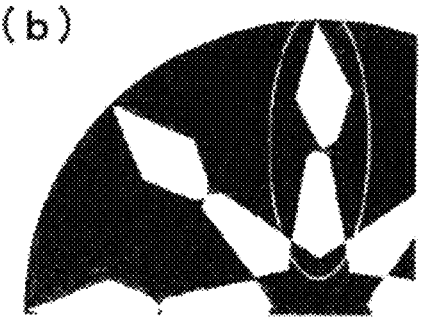
FIG. 14 (c)
FIG. 14 (d)
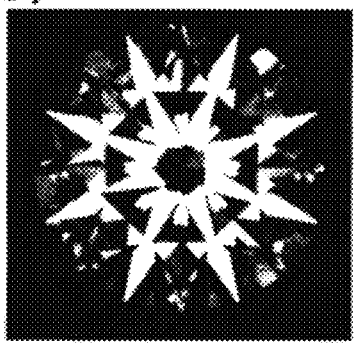
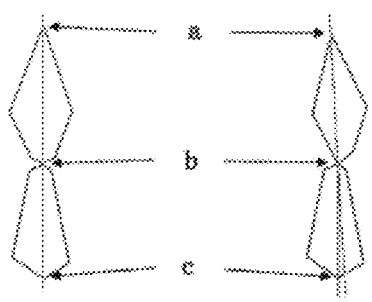
FIG. 14 (e)
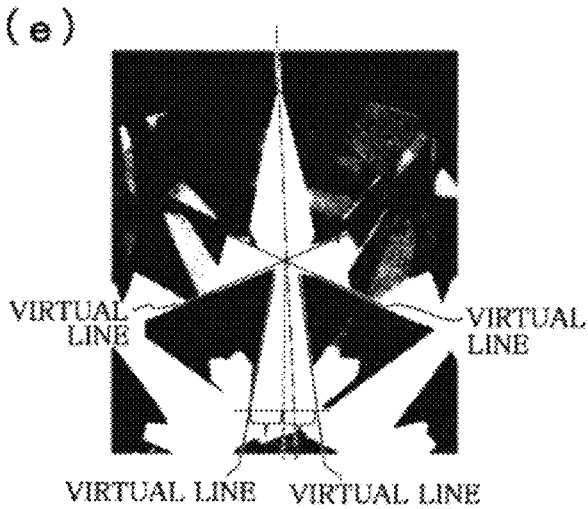

US 9,652,837 B2

METHOD OF DETERMINING QUALITY OF HEART AND CUPID OPTICAL EFFECTS OF DIAMOND DEVICE THEREFOR

TECHNICAL FIELD

The present invention relates to a method and device for determining the quality of Heart & Cupid® optical effects of a round brilliant cut diamond (hereinafter, simply referred to as "diamond"), which is a determination object, enabling the quality of the Heart & Cupid optical effects of the diamond to be objectively determined using program software on the basis of Heart & Cupid images obtained by one of a method of creating the Heart & Cupid images by computer graphics (hereinafter, referred to as "CG") on the basis of the dimensions obtained by measuring the diamond using a dimension measuring device or a method of obtaining the Heart & Cupid images by directly imaging (referred to as "photographing") the diamond using a CCD camera.

BACKGROUND ART

In the conventional quality determination of the Heart & Cupid optical effects of the diamond, a gemologist has determined the quality of a gem in sensory terms according to a unique criterion for determination on the basis of eight heart images and eight cupid images taken by a CCD camera.

Moreover, as another conventional technique, there is a technique described in Patent Document 1.

The technique is a gem appraising device including: a gem illumination unit, having an illuminated space in which a gem to be appraised is arranged, which illuminates a gem arranged in the illuminated space; holding means which holds the gem in such a way that the posture of the gem is variable in the illuminated space of the gem illumination unit; a light source which generates light impinging on the illuminated space of the gem illumination unit; an enlarging optical system which takes in a reflected light of the gem illuminated in the gem illumination unit and forms an enlarged image of the gem; imaging means which takes a gem image formed by the enlarging optical system; an image memory which stores a gem image captured from the imaging means; display means which displays at least the gem image; and quality calculation means which calculates at least one piece of quality information out of the polishing state, color hue, clarity, carat, and inclusion state of the gem on the basis of at least one of the position information and the luminance information of the gem image stored in the image memory (Refer to claim 1 of Japanese Patent No. 3392926).

Moreover, there is a gem appraising method including: causing light from a light source to impinge on a gem illumination unit to illuminate a gem arranged inside the gem illumination unit from all angles; capturing image information by imaging the gem from a position opposite to the gem; creating a histogram by measuring a luminance distribution of the gem on the basis of the image information; analyzing a mode value of the histogram and a distribution state to the low luminance side of the mode value; and determining and evaluating the qualities of the shape and the polishing state of the surface of the gem on the basis of the result of analysis (Refer to claim 20 of Japanese Patent No. 3392926).

CITATION LIST

Patent Documents

Patent Document 1: Japanese Patent No. 3392926

SUMMARY OF THE INVENTION

Problems to be Solved by the Invention

Conventionally, a diamond has been imaged by a CCD camera, and a gemologist has determined the quality of the gem in sensory terms on the basis of each of eight heart images and eight cupid images, and therefore there has been a drawback such that the subjective view of the gemologist enters into the determination, by which the determination depends on a difference in the years of experience of the gemologist, the level of skill, or the like.

Means for Solving the Problems

Moreover, in Patent Document 1, it is an object of the invention to provide a gem appraising device and a method therefor capable of easily achieving an extremely reliable gem appraisement on the basis of objective data independently of the determination of a skilled gemologist. In Patent Document 1, however, it is only described that arbitrary quality information, such as cut, color, clarity, carat, the surface polishing state, inclusions, or the like of a gem, is calculated (See paragraph[0042] of the specification), and there is no description of a specific criterion for determination on each of the eight heart images and eight cupid images of the diamond intended by the present invention and no description of suggesting the same.

It is an object of the present invention to provide a method of determining the quality of Heart & Cupid optical effects of a diamond and a device therefor, capable of objectively determining the quality of the Heart & Cupid optical effects on the basis of the same determination criterion using determination software in both of a case where the diamond is directly imaged by a CCD camera and the quality of the Heart & Cupid optical effects of the diamond is determined on the basis of the obtained Heart & Cupid images and a case where data obtained by measuring the diamond using a dimension measuring device is read out by CG and the quality of the Heart & Cupid optical effects of the diamond is determined on the basis of the obtained Heart & Cupid images.

Furthermore, it is an object of the present invention to provide a method of determining the quality of Heart & Cupid optical effects of a diamond and a device therefor, capable of converting into numbers the entire and individual modes of the symmetry, the size of the shape of each heart and cupid, mutual balance, misregistration, and the like with respect to each of eight heart images and eight cupid images of the diamond so as to quantitatively determine the quality of the Heart & Cupid optical effects of the diamond and, even in the case of not having a diamond to be determined in quality in hand, capable of determining the quality of the Heart & Cupid optical effects of the same diamond quickly and accurately, independently of place and time, only by transmitting heart images and cupid images previously created by CG with respect to the diamond.

Moreover, in the present invention, with respect to an image based on CG of a diamond, an ID or a symbol identifying the diamond is previously entered into the CG image together with dimension measurement data in the stage of measuring the dimensions of the diamond to be determined in quality by using a dimension measuring device, thereby eliminating a problem that a gemologist appraises the quality of the Heart & Cupid optical effects of the diamond on the basis of a photographed image of a diamond different from the diamond to be determined as in the conventional one. It is therefore an object of the present invention to provide a method of determining the quality of Heart & Cupid optical effects of a diamond and a device therefor, capable of further increasing the reliability of the quality determination of the Heart & Cupid optical effects of the diamond.

According to an aspect of the present invention, there is provided a method of determining the quality of Heart & Cupid optical effects of a diamond, including the steps of: reading out dimensions, which have been obtained by measuring a round brilliant cut diamond with an ID appended using a dimension measuring device, by computer graphics (referred to as "CG") and outputting Heart & Cupid images and the ID or outputting Heart & Cupid images of the diamond taken by a CCD camera and an ID; storing data, such as the symmetry of eight heart marks, variation in the area of a heart, the displacement of the tip portion of each heart, the depth of a slit of each heart, a ratio of right and left shoulder widths relative to the overall width of each heart, a ratio of a distance in a boundary portion between each heart and a V-shaped mark located on the inner side on the radial line of the heart relative to the overall width of the corresponding heart, a ratio between the area of the V-shaped mark and the area of a standard heart, and a ratio between the right-side length of the V-shaped mark and the left-side length of the V-shaped mark, into a computer database; determining the ranking of the quality of the heart marks by performing arithmetic processing of the data; and storing data, such as the symmetry of eight cupid marks, a variation degree obtained from the ratio between the maximum value and the minimum value of each cupid area, whether a straight line connecting the outer tip portion, the intermediate intersection, and the center-side tip of each cupid overlaps another one or has a displacement with an angle, and whether the arrow tip portion of each cupid sharply abuts against a girdle or abuts against the girdle portion with a width, into a computer database and determining the ranking of the quality of the cupid marks by performing arithmetic processing of the data.

A method of determining the quality of Heart & Cupid optical effects of a diamond according to claim 1 includes the step of determining quality ranking by converting into numbers the symmetry of each heart mark and cupid mark, the displacement of each shape, and the displacement in a distance between a heart mark and a V-shaped mark, reading the data converted into numbers by a computer, and performing determination processing by using the computer, wherein the ranking determination includes three determined area means where an approved area, a disapproved area, and approved and disapproved areas are present or two determined area means where an approved area and a disapproved area are present.

The method of determining the quality of Heart & Cupid optical effects of the diamond in which the diamond is imaged by a CCD camera according to claim 1 or 2 includes the step of determining the quality by reading out the number of contrasts of the heart mark images and the cupid mark images using the computer and performing determination processing using the computer.

A device for determining the quality of Heart & Cupid optical effects of a diamond according to the present invention includes: means for obtaining Heart & Cupid images by photographed images taken by a CCD camera or means for obtaining Heart & Cupid images by reading out dimensions obtained by measuring regions of the patterns of light emitted to the diamond, which has been polished in particular proportions, using a dimension measuring device by computer graphics (CG); means for reading out the same ID as one appended to the diamond into the photographed image or the CG image; means for storing the Heart & Cupid images into a computer database; an arithmetic processing device of a computer which performs arithmetic processing with respect to determination items from Heart & Cupid images managed by ID on the basis of numerical values read from the computer database; and display means for determining the quality of the diamond on the basis of the arithmetic processing.

Advantageous Effect of the Invention

The present invention provides a method of determining the quality of Heart & Cupid optical effects of a diamond and a device therefor, capable of objectively determining the quality of the Heart & Cupid optical effects according to the same determination criterion using determination software in both of a case where the diamond is directly imaged by a CCD camera and the quality of the Heart & Cupid optical effects of the diamond is determined on the basis of the obtained Heart & Cupid images and a case where data obtained by measuring the diamond using the dimension measuring device is read out by CG and the quality of the Heart & Cupid optical effects of the diamond is determined on the basis of the obtained Heart & Cupid images.

Moreover, the present invention is capable of determining the quality of Heart & Cupid optical effects of a diamond qualitatively by converting into numbers the entire and individual modes of the symmetry, the size of the shape of each heart and cupid, mutual balance, misregistration, and the like with respect to each of eight heart images and eight cupid images of the diamond, storing the data into a computer database, and reading out the data.

Even in the case of not having a diamond, with an ID, to be determined in quality in hand, the present invention is capable of quickly and accurately determining the quality of Heart & Cupid optical effects of the diamond with the same ID appended thereto, independently of place and time, via the Internet line since the computer database stores heart images and cupid images having the same ID previously created by CG with respect to the diamond.

Furthermore, in the present invention, the heart images and cupid images having an ID, which have been created by reading out the numerical values by CG wherein the numerical values have been obtained by measuring a diamond to be determined with the same ID appended using the dimension measuring device, correspond to the heart images and cupid images of the diamond to be determined on one-to-one basis, thereby eliminating a problem that a gemologist appraises the quality of the diamond on the basis of an incorrect photographed image as in the conventional one and further increasing the reliability of the quality determination of the Heart & Cupid optical effects of the diamond.

BRIEF DESCRIPTION OF THE DRAWINGS

FIG. 1(a) illustrates a determination result of approval; and FIG. 1(b) illustrates a determination result of disapproval with places causing the determination of disapproval indicated by red circles (for convenience, indicated by black and white representation in the diagram).

FIG. 2(a) illustrates heart mark images; and FIG. 2(b) illustrates cupid mark images.

FIG. 3(a) illustrates heart mark images; and FIG. 3(b) illustrates cupid mark images.

FIG. 6(a) is a diagram illustrating a displacement of the tip portion of each heart mark of the diamond according to the present invention; FIG. 6(b) is a diagram illustrating an example in which the tip portion of the heart mark does not focus on one point; FIG. 6(c) is a diagram illustrating an example in which the tip portion of the heart mark focuses on one point; FIG. 6(d) is a quality determination chart with rank A to rank C illustrating displacement degrees from the position where the tip portion of the heart focuses on one point; and FIG. 6(e) is a table illustrating a quality determination result of the displacement of a heart tip portion displayed by a determination result display device.

FIGS. 8(a) and 8(b) are explanatory diagrams illustrating measurement regions for determining the quality of the widths of the right and left shoulder portions of each heart mark of the diamond according to the present invention; FIG. 8(c) is a quality determination chart illustrating the quality of the widths of the right and left shoulder portions of each heart mark image; and FIG. 8(d) is a table illustrating a quality determination result of the heart shoulder portions displayed by the determination result display device.

FIGS. 9(a) and 9(b) are diagrams illustrating the quality of a distance in a boundary portion between each heart mark of the diamond and a V-shaped mark located in the direction of the tip of the heart mark according to the present invention; FIG. 9(c) is a quality determination chart illustrating the quality of the distance in the boundary portion between each heart mark and the V-shaped mark located in the direction of the tip of the heart mark; and FIG. 9(d) is a table illustrating a quality determination result of the distance in the boundary portion displayed by the determination result display device.

FIGS. 10(a) to 10(c) are diagrams illustrating the quality determination of variation of the regions in the size of each V-shaped mark located on the inner side of the tip portion of the heart mark of the diamond according to the present invention; FIG. 10(d) is a quality determination chart of the V-shaped mark; and FIG. 10(e) is a table illustrating a quality determination result in the size of the V-shaped marks displayed by the determination result display device.

FIGS. 11(a) to 11(c) are diagrams illustrating the quality determination of the balance of the right and left length of each V-shaped mark of the diamond according to the present invention; FIG. 11(d) is a quality determination chart illustrating the quality of the V-shaped mark; and FIG. 11(e) is a table illustrating a quality determination result of the right and left lengths of the V-shaped marks displayed by the determination result display device.

FIGS. 14(a), 14(b), 14(c), 14(d), and 14(e) are diagrams illustrating the modes of the displacement of the arrow tip of a cupid.

MODE FOR CARRYING OUT THE INVENTION

Figure 1:
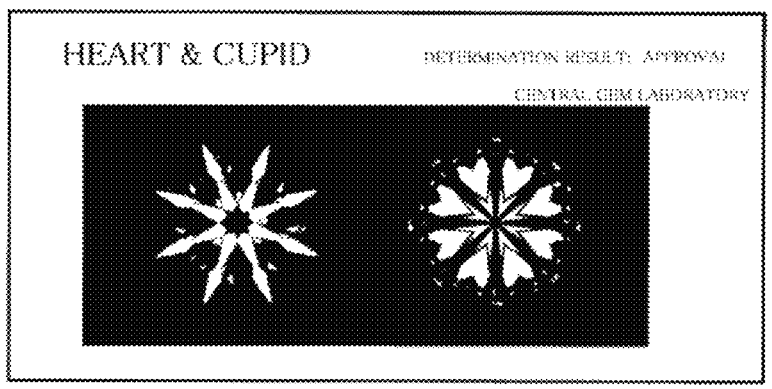
FIG. 1 is a diagram illustrating CG or photographed Heart & Cupid images of a diamond according to the present invention.
Figure 1:
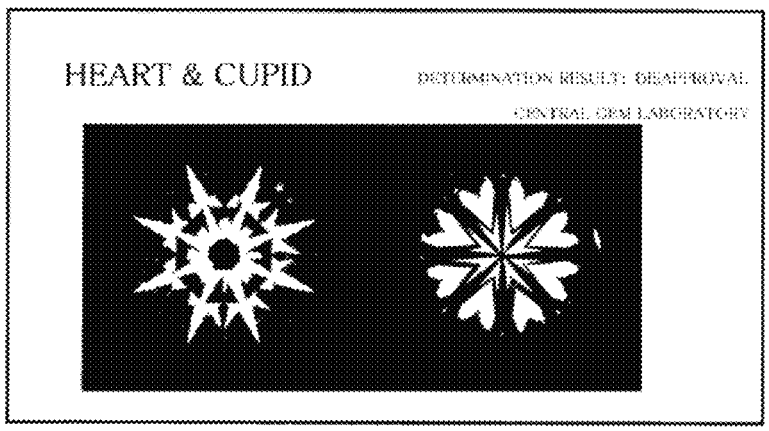
Figure 2:
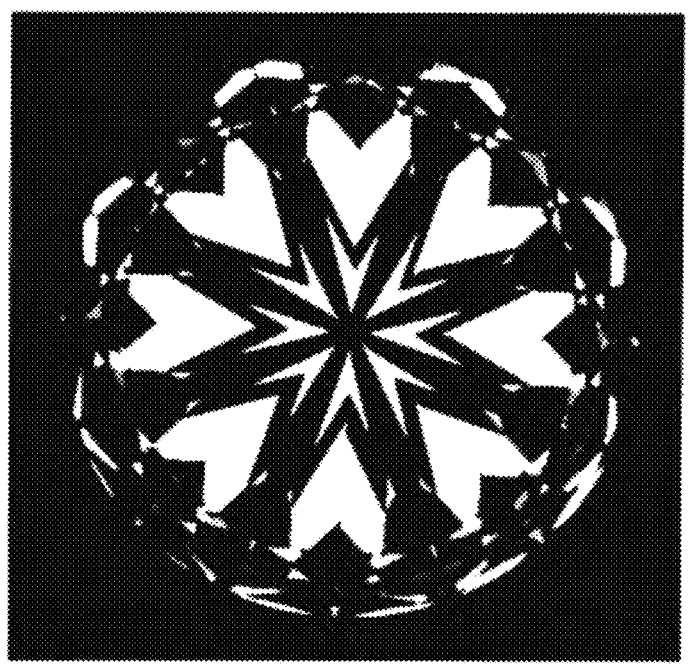
FIG. 2 is a diagram illustrating Heart & Cupid mark images by CG to be determined in the quality of the Heart & Cupid optical effects of the diamond according to the present invention.
Figure 2:
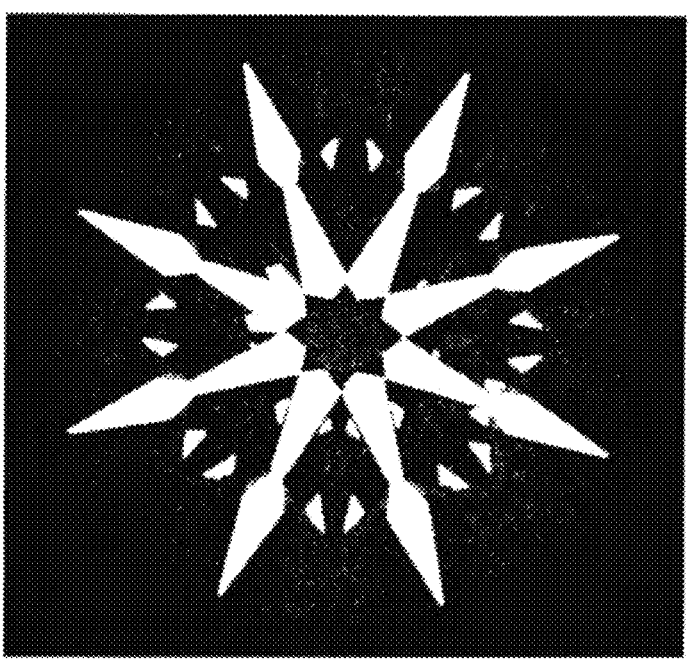
Figure 3:
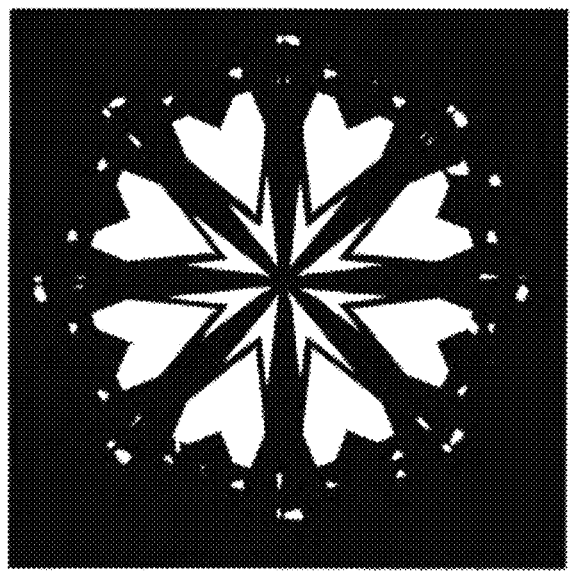
FIG. 3 is a diagram illustrating photographed Heart & Cupid mark images to be determined in the quality of the Heart & Cupid optical effects of the diamond according to the present invention.
Figure 3:
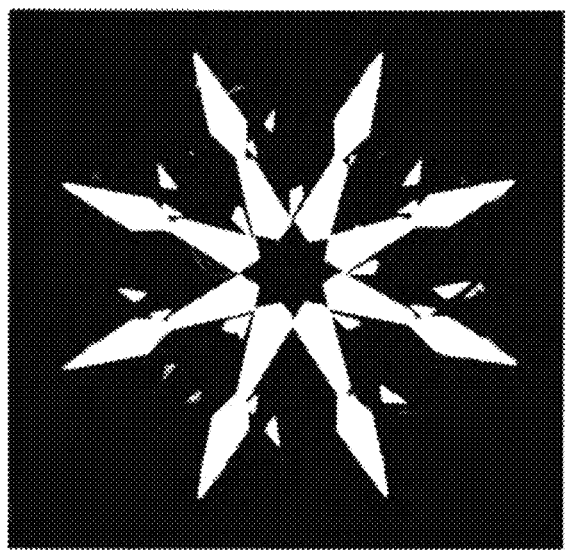

Hereinafter, an embodiment of the present invention will be described with reference to appended drawings. First, the outline of a CG image is as described below.

For a round brilliant cut diamond 1 (hereinafter, simply referred to as "diamond"), the respective parts are accurately measured in dimensions and angle with respect to the shape of the diamond viewed from directly above on the crown (not illustrated) side which is the upper part of a girdle (not illustrated) including a table (not illustrated) and the shape of the diamond viewed from the pavilion (not illustrated) side which is the lower part of the girdle. Light impinging on, for example, the table top of the diamond partially becomes reflected light on the surface and diverges outside and the remaining light becomes refracted light refracted by the inside of the diamond and then is refracted on the pavilion surface and emitted in the atmosphere. The refracted light inside the diamond may be totally reflected according to the angle of incidence in some cases. Although this embodiment describes a case of calculation with a value of 2.417 as the refractive index of the diamond, the refractive index is not necessarily limited to this value. Although this embodiment describes a case where, for example, the luminous flux impinging on the surface from directly above on the table and crown side is formed of 1000 beams (1µ) per 1 mm in the range of the end to end of the diamond, the number of beams is not necessarily limited to this value. For example, if the part on the table and crown side is gridironed from directly above in the micron order in horizontal and vertical directions and the luminous flux is caused to impinge on the diamond in the direction vertical to the surface, heart images can be obtained by simulating the light trace of the luminous flux. Cupid images can be obtained by causing the luminous flux to impinge on the diamond from the pavilion side on the opposite side.

A method of determining the quality of Heart & Cupid optical effects of a diamond according to the present invention includes the process of measuring the dimensions of a diamond 1, which is to be determined, with an ID appended by using a dimension measuring device 5 and reading out the measurement result by computer graphics (referred to as "CG") to obtain Heart & Cupid images with the ID appended or the process of taking Heart & Cupid images of the diamond by using a CCD camera. Subsequently, with respect to eight heart marks, the quality determination method undergoes the process of reading out the symmetry, the variation in the area, the displacement of a tip portion, the depth of a slit, a ratio of right and left shoulder widths relative to the overall width, a ratio of a distance in a boundary portion between each heart mark and the V-shaped mark located on the inner side on the radial line of the heart mark relative to the overall width of the corresponding heart, a ratio between the area of the V-shaped mark and the area of a standard heart mark, and a ratio between the right-side length of the V-shaped mark and the left-side length of the V-shaped mark by using a computer, performing arithmetic processing of the numerical values read out by the computer, and determining the ranking of the quality of the marks. Subsequently, with respect to eight cupid marks, the quality determination method undergoes the process of reading out the symmetry, a variation degree obtained from the ratio between the maximum value and the minimum value of the area, whether a straight line connecting the outer tip portion, the intermediate intersection, and the center-side tip matches the line to be determined or there is a displacement with an angle between the lines, and whether the arrow tip portion sharply abuts against the girdle or abuts against the girdle portion with a width by a computer and determining the ranking of the quality by performing determination processing of the read numerical values by using the computer.

Figure 4:
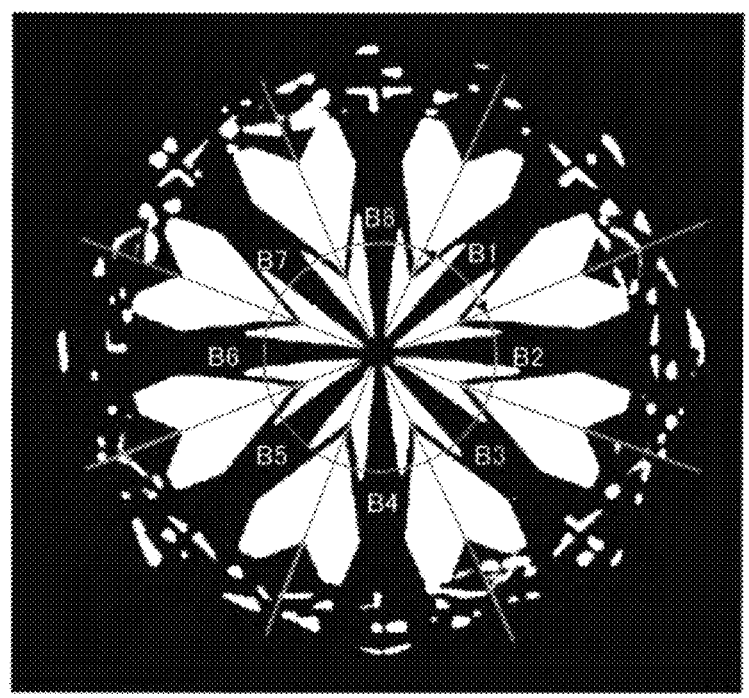
FIG. 4(a) is a diagram illustrating angles B1 to B8 each between the centers of heart marks adjacent to each other for determining the quality of symmetry of eight heart mark images of the diamond according to the present invention.
FIG. 4(b) is a quality determination chart with rank A (approval) and rank C (disapproval) illustrating the quality of the symmetry obtained by arithmetic processing after reading out the absolute value of the total sum of values obtained by subtracting 45 degrees from each angle between the centers of heart marks adjacent to each other by using a computer.
Figure 4:
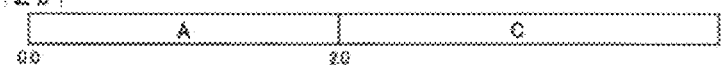

Referring to FIG. 4, there is illustrated heart mark images created by CG to be determined in the quality of Heart & Cupid optical effects of the diamond according to the present invention: FIG. 4(a) illustrates angles B1 to B8 each between the centers of heart marks adjacent to each other for use in determining the quality of the symmetry of eight heart mark images of the diamond according to the present invention; and FIG. 4(b) is a quality determination chart with rank A and rank C illustrating the quality determination of the symmetry obtained from the absolute value of the total sum of values obtained by subtracting 45 degrees from each angle between the centers of heart marks adjacent to each other.

The present invention includes determination means for determining the quality of the Heart & Cupid optical effects of the diamond, namely a determination result display device, and the determination result is obtained according to the number of bars among the eight bars displayed in the A, B, or C zone or in the A or C zone (the bars are not illustrated in the embodiment and the appended drawings). In FIG. 4, if the eight heart mark images are each bilaterally symmetrical, eight bars appear in the range of rank A in the chart and the determination is approval in rank A on the quality determination table. If there is at least one heart mark image which is not bilaterally symmetrical, one bar appears in the range of rank C in the chart and the determination is disapproval in rank C. In this manner, each of the eight bars appears in any one of the ranges of A, B, and C in the chart in the determination, and the quality of the diamond is determined according to the number of bars in each range. Also in the subsequent drawings, the determination is performed in the same manner. It is, however, additionally noted that the determination is approval if one to three bars appear in the range of B in the chart and the determination is disapproval if four or more bars appear in the range of B.

Items to be determined are: (1-1) symmetry (the quality of the symmetry of a heart); (1-2) area variation; (1-3) displacement of a tip portion; (1-4) the depth of a slit; (1-5) shoulder widths; (1-6) a distance in a boundary portion between a heart mark and a V-shaped mark; (1-7) variation in the area of a V-shaped mark; and (1-8) unbalance of a V-shaped mark, with respect to the heart marks.

First, with respect to the quality of the symmetry of a heart, an angle of 45 degrees is standard for the angles B1 to B8 in FIG. 4(a). The sum $|\Sigma\beta|$ of the following is calculated: B1−45=|β1|; B2−45=|β2|; B3−45=|β3|; B4−45=|β4|; B5−45=|β5|; B6−45=|β6|; B7−45=|β7|; and B8−45=|β8|. The larger the value $\Sigma\beta$ is, the worse the symmetry is. The threshold value of $|\Sigma\beta|$, however, is modifiable.

The quality determination of the symmetry illustrated in FIG. 4(b) is represented by a quality determination chart with rank A and rank C. If the value is 0.00 or more to less than 2.00, the symmetry of the heart belongs to rank A and is determined to be approved. If the value is 2.00 or more, the symmetry belongs to rank C and is determined to be disapproved. The numerical value ranges of rank A and rank C are not limited to this embodiment.

Figure 5:
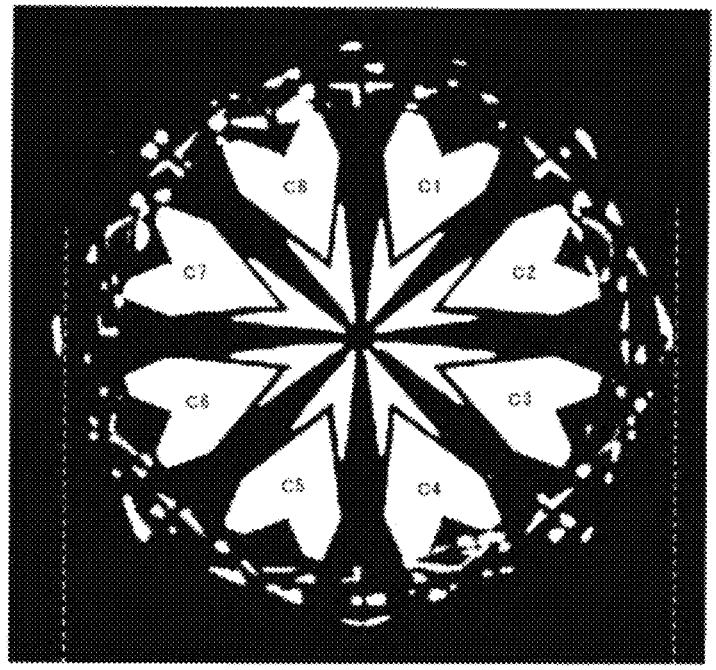
FIG. 5(a) is a diagram illustrating areas C1 to C8 of the heart marks of the diamond according to the present invention for use in determining whether the variation degree of the images and the size of each heart image are appropriate.
FIG. 5(b) illustrates that the area of one heart mark is enclosed by an outline.
FIG. 5(c) is a quality determination chart with rank A (approval) and rank C (disapproval) illustrating whether the area of each heart mark is appropriate in size.
Figure 5:
Figure 5:
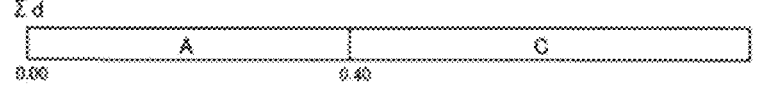
Figure 7:
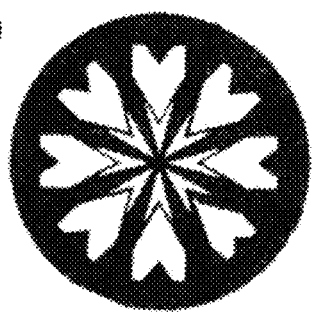
FIGS. 7(a) to 7(f) are explanatory diagrams illustrating the depth of a slit of each heart mark of the diamond according to the present invention.
FIG. 7(g) is a quality determination chart illustrating the quality of Heart & Cupid optical effects of the diamond obtained from the depth of the slit of each heart mark image of the diamond according to the present invention.
FIG. 7(h) is a table illustrating a quality determination result of the depth of the slit of the heart displayed by the determination result display device.
Figure 7:
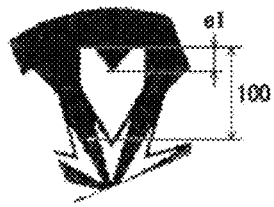
Figure 7:
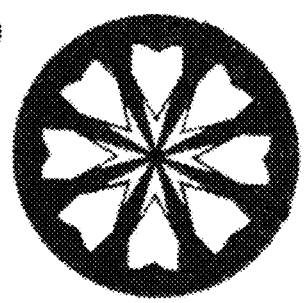
Figure 7:
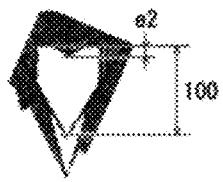
Figure 7:
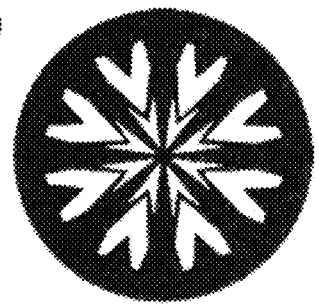
Figure 7:
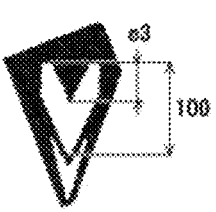
Figure 7:

FIG. 5(a) is a diagram illustrating the areas C1 to C8 of the heart marks of the diamond according to the present invention for use in determining whether the variation degree of each heart image and the size of each heart image are appropriate. FIG. 5(b) illustrates the region in which the area of one heart mark is enclosed by an outline; and FIG. 5(c) is a quality determination chart with rank A and rank C illustrating whether the area of each heart mark is appropriate in size. If the value is 0.00 or more to less than 0.40, the area of the heart belongs to rank A and is determined to be appropriate and therefore approved. If the value is 0.40 or more, the area of the heart belongs to rank C and is determined to be disapproved.

The area of each heart enclosed by a red line (represented by a black line in this diagram for convenience of drawing) is indicated by each of C1 to C8. It is assumed that the maximum value of each heart area is Cmax, the minimum value of each heart area is Cmin, and Cmax/Cmin=C is satisfied. If the C value is 1, there is no variation in the size of the heart mark. This embodiment describes a case where this item is determined to be approved if the C value is between 1.00 and 1.11 and to be disapproved if the C value is 1.11 or more. The variation degree of the area of each heart is obtained from the values of the maximum value Cmax and the minimum value Cmin, but it is not determined whether each heart has an appropriate size. Therefore, the determination of whether each heart has an appropriate size is achieved by calculating an expression 1, such that the determination is made on the basis of a difference from a factor obtained by [C of the most standard heart]/(the entire area (standard))]×100. For this value, a certain ideal numerical value is settable, independently of the size of the diamond. In sensory terms, this value is [2.91 to 3.29] and an average value is in the order of 3.18 as a standard value. In expression 1, however, the calculation is made using the standard value of 3.2. The closer to zero the numerical value Σd, which has been obtained by the expression 1 of C1 to C8, is, the closer to the standard value the size of the heart is.

$$\underline{\begin{array}{l} 3.2 - \dfrac{C1}{\text{(entire area (diamond to be evaluated))}} \times 100 = d1 \\ 3.2 - \dfrac{C1}{\text{(entire area (diamond to be evaluated))}} \times 100 = d1 \\ \vdots \\ 3.2 - \dfrac{C1}{\text{(entire area (diamond to be evaluated))}} \times 100 = d1 \end{array}}_{\Sigma d} \quad \text{[Equation 1]}$$

FIG. 6(a) is a diagram illustrating a displacement of the tip portion of each heart mark of the diamond according to the present invention. FIG. 6(b) illustrates an example that the tip portion of the heart mark does not focus on one point. FIG. 6(c) illustrates an example in which the tip portion of the heart mark focuses on one point. FIG. 6(d) illustrates the displacement degrees from the position where the tip portion of the heart focuses on one point by using a quality determination chart with rank A to rank C. FIG. 6(e) is a table illustrating a quality determination result of the displacement of a heart tip portion displayed by the determination result display device.

Comparing FIG. 6(b) with FIG. 6(c), the tip portion of the heart does not focus on one point in FIG. 6(b). If a1 is the displacement of the tip portion and A is the overall length of the heart, an equation a1/A1=A is satisfied. Where A1 is 1, it is assumed that the determination is approval in a range where a1 is 0.00 or more to less than 0.06, that approval and disapproval are mixed as the determination in a range where a1 is 0.06 or more to less than 0.17, and that the determination is disapproval in a range where a1 is 0.17 or more. The determination table illustrates that the determination is approval if there are eight heart marks with no displacement in the heart tip portions, the determination is disapproval if there is at least one heart mark belonging to the C zone in the chart, the determination is approval if there are one to three heart marks belonging to the B zone in the chart, and the determination is disapproval if there are four or more heart marks belonging to the B zone in the chart.

FIGS. 7(a) to 7(f) are explanatory diagrams illustrating the depth of the slit of each heart mark of the diamond according to the present invention. With respect to one heart mark illustrated in FIG. 7(a), the ratio of the depth of the slit relative to the overall length of the heart mark is e1/100 assuming that the depth of the slit is e1 and the overall length of the heart mark is 100 in FIG. 7(b). Similarly, the ratio is e2/100 in FIG. 7(d) and is e3/100 in FIG. 7(f). The ratio of the depth of the slit of a standard heart mark is 0.229. Therefore, the determination is approval in rank A if the ratio of the depth of the slit of the heart is, as illustrated in FIG. 7(g), 0.20 or more to less than 0.37, approval and disapproval are mixed as the determination of rank B if the ratio is 0.14 or more to less than 0.20 or is 0.37 or more to less than 0.46, and the determination is disapproval in rank C if the ratio is 0.00 or more to less than 0.14 or is 0.46 or more. The determination table illustrates that the determination is approval if there are eight heart marks each having the depth of the slit of the heart determined to be good, the determination is disapproval if there is at least one heart mark belonging to the C zone in the chart, the determination is approval if there are one to three heart marks belonging to the B zone in the chart, and the determination is disapproval if there are four or more heart marks belonging to the B zone in the chart.

FIGS. 8(a) and 8(b) are explanatory diagrams illustrating measurement regions for determining the quality of the widths of the right and left shoulder portions of each heart mark of the diamond according to the present invention. FIG. 8(c) illustrates the quality of the widths of the right and left shoulder portions of each heart mark image by using a quality determination chart.

As illustrated in FIG. 8(a), it is assumed that the widths of the respective hearts are A1, A2, - - - A7, and A8, the left shoulder width of one heart is a1 and the right shoulder width thereof is a2, and equations (a1/A1)=k1 and (a2/A1)=k2 are satisfied. Hereinafter, it is sequentially assumed that the following equations are satisfied: (a1/A2)=k3; (a2/A2)=k4; (a1/A8)=k15; and (a2/A8)=k16.

FIG. 8(c) is a quality determination chart illustrating the widths of the right and left shoulder portions of each heart mark image. The determination is approval in rank A if the value is 0.10 or more to less than 0.30, approval and disapproval are mixed as the determination of rank B if the value is 0.01 or more to less than 0.10 or is 0.30 or more to less than 0.53, and the determination is disapproval in rank C if the value is 0.00 or more to less than 0.01 or is 0.53 or more. FIG. 8(d) is a table illustrating a quality determination result of the heart shoulder portions displayed by the determination result display device. The determination table illustrates that the determination is approval if there are eight heart marks each having the widths of the heart shoulder portions determined to be good, the determination is disapproval if there is at least one heart mark belonging to the C zone in the chart, the determination is approval if there are one to three heart marks belonging to the B zone in the chart, and the determination is disapproval if there are four or more heart marks belonging to the B zone in the chart.

FIGS. 9(a) and 9(b) are diagrams illustrating the quality of a distance in a boundary portion between each heart mark of the diamond and the V-shaped mark located in the direction of the tip of the heart mark according to the present invention. FIG. 9(c) is a quality determination chart illustrating the quality of the distance in the boundary portion between each heart mark and the V-shaped mark located in the direction of the tip of the heart mark. FIG. 9(d) is a table illustrating a quality determination result of the distance in the boundary portion displayed by the determination result display device.

Calculation is made on (a1/A1) where a1 is the distance in the boundary portion between each heart mark and the V-shaped mark located in the direction of the tip of the heart mark and A1 is the width of the heart mark. Assuming that A1 is 1 and if a1 is 0.02 or more to less than 0.15, the determination is approval in rank A. If a1 is 0.01 or more to less than 0.02 or is 0.15 or more to less than 0.33, approval and disapproval are mixed. If a1 is 0.00 or more to less than 0.01 or is 0.33 or more, the determination is disapproval in rank C. On the determination table, the determination is approval if there are eight heart marks each having the distance in the boundary portion determined to be good, the determination is disapproval if there is at least one heart mark belonging to the C zone in the chart, the determination is approval if there are one to three heart marks belonging to the B zone in the chart, and the determination is disapprove if there are four or more heart marks belonging to the B zone in the chart.

FIGS. 10(a) to 10(c) are diagrams illustrating the quality determination of the variation in the lengths in the size of a V-shaped mark located on the inner side of the tip portion of each heart mark of the diamond according to the present invention, and FIG. 10(d) illustrates the quality of the size of the V-shaped mark by using a quality determination chart. FIG. 10(e) is a table illustrating a quality determination result in the size of the V-shaped marks displayed by the determination result display device.

Eight V-shaped marks are denoted by b1, b2, b3, b4, b5, b6, b7, and b8. Calculation is made on (b1/A), (b2/A), - - - (b7/A), (b8/A) assuming that A is the area of a standard heart mark in the entire image of the diamond and that b1 to b8 are the areas of the V-shaped marks of the diamond to be checked relative to the area A. The threshold values are assumed to be variable. If the value is 0.13 or more to less than 0.25, the determination is approval in rank A. If the value is 0.02 or more to less than 0.13 or is 0.25 or more to less than 0.42, approval and disapproval are mixed in rank B. If the value is 0.00 or more to less than 0.02 or is 0.42 or more, the determination is disapproval in rank C. The determination table illustrates that the determination is approval if there are eight heart marks each having the size of the V-shaped mark determined to be good, the determination is disapproval if there is at least one heart mark belonging to the C zone in the chart, the determination is approval if there are one to three heart marks belonging to the B zone in the chart, and the determination is disapproval if there are four or more heart marks belonging to the B zone in the chart.

FIGS. 11(a) to 11(c) are diagrams illustrating the quality determination of the balance in the lengths of the right and left regions of each V-shaped mark of the diamond according to the present invention, and FIG. 11(d) is a quality determination chart illustrating the quality of the V-shaped mark. FIG. 11(a) illustrates a distance between the oblique side of a heart mark and the V mark located on the inner side of the heart mark. FIG. 11(b) is a diagram illustrating an example of a case where the tip portions of the V-shaped mark are even. FIG. 11(c) is a diagram illustrating an example of a case where the right and left tip portions of the V-shaped mark are uneven. It is assumed that A is the left-side length of a V-shaped mark, B is the right-side length of the V-shaped mark, and B/A=α is satisfied. FIG. 11(d) illustrates the quality of the right and left lengths of the V-shaped mark by using a determination chart. FIG. 11(e) is a table illustrating a quality determination result of the right and left lengths of the V-shaped marks displayed by the determination result display device. If the value α is 0.80 or more to less than 1.20, the determination is approval in rank A. If the value α is 0.00 or more to less than 0.70 or is 1.30 or more, the determination is disapproval in rank C. If the value α is 0.70 or more to less than 0.80 or is between 1.20 and 1.30, the quality is determined to be rank B. On the determination table, the determination is approval if there are eight heart marks each having a V-shaped mark with the right and left lengths determined to be good, the determination is disapproval if there is at least one heart mark belonging to the C zone in the chart, the determination is approval if there are one to three heart marks belonging to the B zone in the chart, and the determination is disapprove if there are four or more heart marks belonging to the B zone in the chart.

Figure 12:
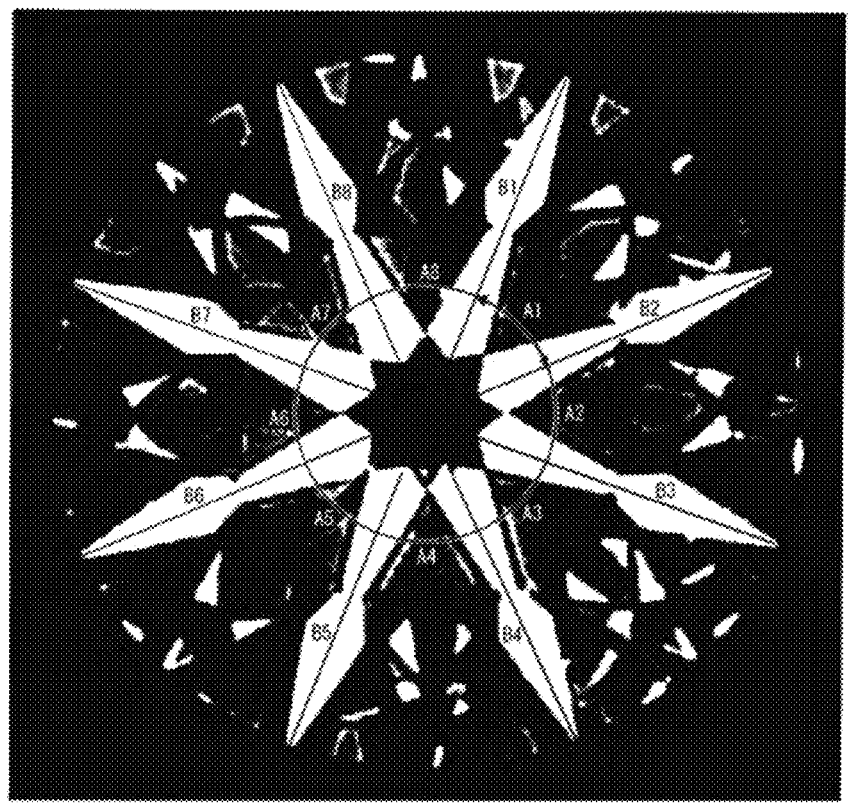
FIG. 12(a) is a diagram illustrating the quality determination of the symmetry and length of each cupid of the diamond according to the present invention.
FIG. 12(b) is a quality determination chart illustrating the quality of the symmetry of the cupid.
FIG. 12(c) is a quality determination chart illustrating the quality of the length of the cupid.
Figure 12:
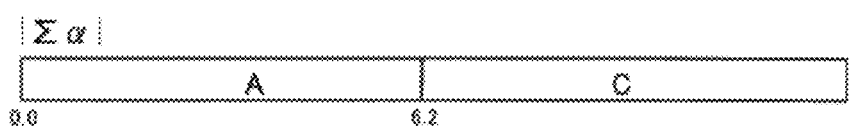
Figure 12:
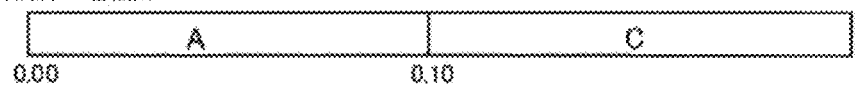

FIG. 12(a) is a diagram illustrating the quality determination of the symmetry (angle and length) of each cupid of the diamond according to the present invention and FIG. 12(b) illustrates the quality determination of the symmetry of the cupid by using a chart. FIG. 12(c) illustrates the quality determination of the length of the cupid by using a chart.

Assuming that the lines extending from the arrow tip to the center of the arrow of the eight cupids are B1, B2, B3, - - - B8 and that the angles between cupids adjacent to each other are A1 (angle between B1 and B2), A2, A3, - - -, A8, equations A1−45=|α1|, A2−45=|α2|, A3−45=|α3|, - - -, A7−45=|α7|, A8−45=|α8| are calculated. The larger the total |Σα| of α1 to α8 is, the worse the symmetry is. Note that, however, the threshold value of |Σα| is variable. In the quality determination chart illustrated in FIG. 12(b), the determination is approval in rank A if the value is 0.00 or more to less than 6.20 and the determination is disapproval in rank C if the value is 6.20 or more.

It is assumed that the maximum value of the length of the cupid is Bmax and the minimum value of the length is Bmin. The closer to zero the value of Bmax−Bmin is, the less the variation in the length of the cupid is. As to the determination of the variation in the length of the cupid illustrated in FIG. 12(c), the determination is approval in rank A if the value is 0.00 or more to less than 0.10 which belongs to the A zone in the chart, and the determination is disapproval in rank C if the value is 0.10 or more which belongs to the C zone in the chart.

Figure 13:
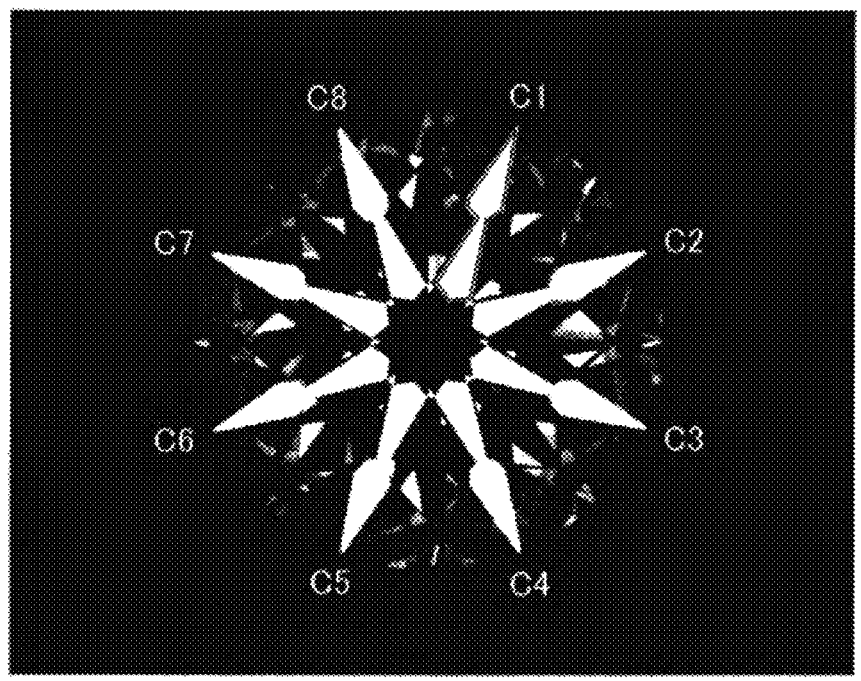
FIG. 13(a) is a diagram illustrating the variation in the area of the cupid of the diamond according to the present invention.

FIG. 13(a) is a diagram illustrating the variation in the area of each cupid of the diamond according to the present invention. The variation in the area of each cupid relative to the entire area of the diamond will be described below. C1 to C8 are assumed to be the areas of the cupids each enclosed by a red line (indicated by a black line for convenience of drawing). It is assumed that the maximum value of the area of the cupid is Cmax and that the minimum value thereof is Cmin. Equation Cmax/Cmin=C is assumed. If this C value is 1, it can be said that there is no variation. If the C value is 1.00 or more to less than 1.34, the determination is approval. If the C value is 1.34 or more, the determination is disapproval.

FIGS. 14(a), 14(b), 14(c), 14(d), and 14(e) are diagrams illustrating the modes of the displacement of the arrow tip of a cupid. The displacement of the arrow tip of each cupid is evaluated as described below. If a virtual line connecting the tip a and an intersection b of each cupid and a virtual line connecting the intersection b and the tip c of the cupid form a straight line, the determination is approval. If an angle between the virtual line connecting the tip a and the intersection b and the virtual line connecting the intersection b and the tip c is 1.5 degrees or more, the determination is disapproval. Note that, however, it is possible to prepare a table for setting a criterion for determination with the angle of 1.5 degrees and the criterion can be modified. To find the angle, the tip portion of the cupid is often ambiguous. Accordingly, virtual lines are drawn as illustrated in FIG.

14(e) to find an angle between a dotted line, which equally divides the cupid at the center line, and a dashed-dotted line as a determination numerical value.

Figure 15:
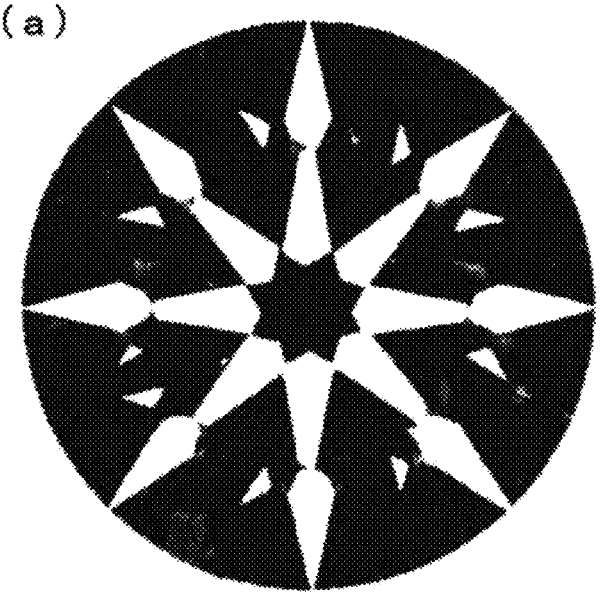
FIGS. 15(a), 15(b), and 15(c) are diagrams illustrating the modes of the sharpness degree of the arrow tip portion of a cupid of the diamond according to the present invention.
Figure 15:
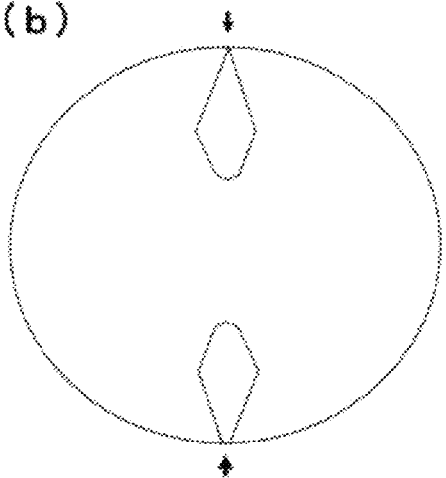
Figure 15:
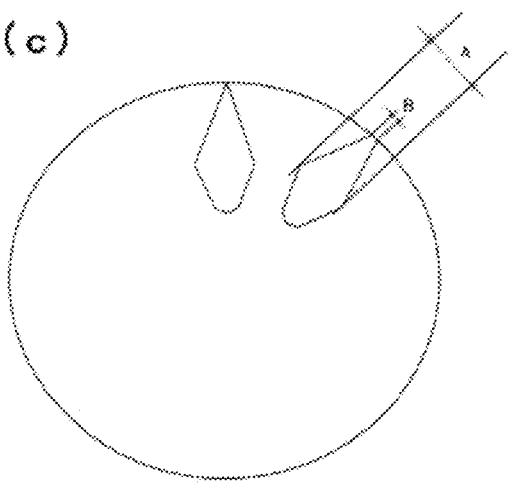

FIGS. 15(a), 15(b), and 15(c) are diagrams illustrating the modes of the sharpness degree of the arrow tip portion of the cupids of the diamond according to the present invention. If each tip portion of the arrow of the cupid illustrated in FIG. 15(a) is sharply in contact with the girdle portion as illustrated in the upper part of FIG. 15(b), the determination is approval. To the contrary, if the arrow tip portion of the cupid is in contact with the girdle portion in such a way that the tip portion has a width as illustrated in the lower part of FIG. 15(b), the determination is disapproval. As illustrated in FIG. 15(c), it is assumed that B is the width of the arrow tip portion relative to the width A of the cupid and B/A=α is satisfied. If α is 0.32 or more, the determination is disapproval. Note that, however, the threshold value of α is modifiable.

Figure 16A:
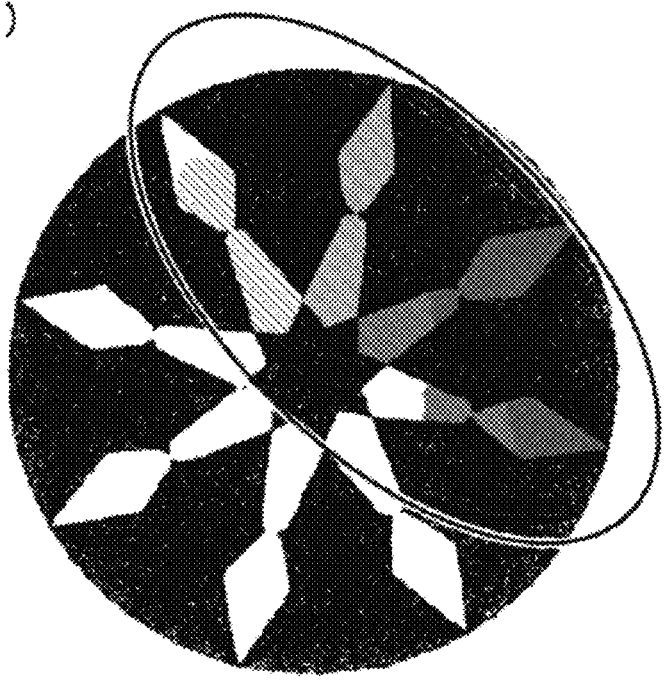
FIGS. 16(a), 16(b), 16(c), 16(d), and 16(e) are diagrams illustrating contrasts in the cupids of the diamond according to the present invention. The contrast in each cupid image is represented by a distance between hatching lines depending on the degree of brightness for convenience.
Figure 16B:
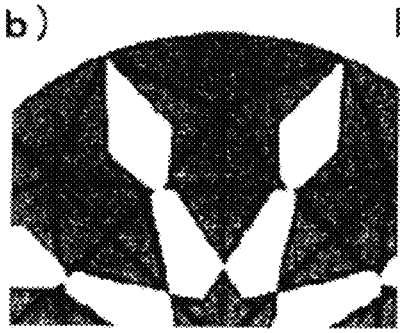
Figure 16C:
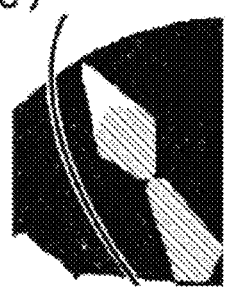
Figure 16D:
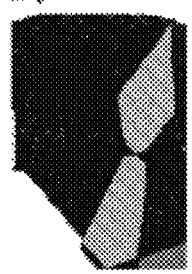
Figure 16E:
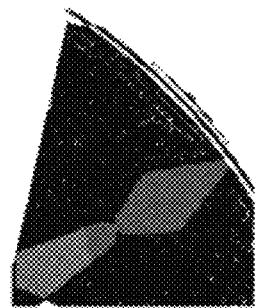

FIGS. 16(a), 16(b), 16(c), 16(d), and 16(e) are diagrams illustrating contrasts in the cupids of the diamond imaged by a CCD camera according to the present invention. FIG. 16(a) is a diagram illustrating a state where a portion representing the contrasts of the cupids is enclosed by an ellipse. FIGS. 16(b) to 16(e) illustrate the states in which the image thresholding of the cupid image is classified into four stages A, B, C, and D according to the brightness: A is a completely white area; B is a slightly grayish area; C is a rather thick grayish area; and D is a completely black area. On the determination table, if there are eight cupid images each having the brightness of A, the determination is approval. If there are one to three cupid images having the brightness of B, the determination is approval. If there are four or more cupid images having the brightness of B, the determination is disapproval. If there is at least one cupid image having the brightness of C or D, the determination is disapproval.

Figure 17:
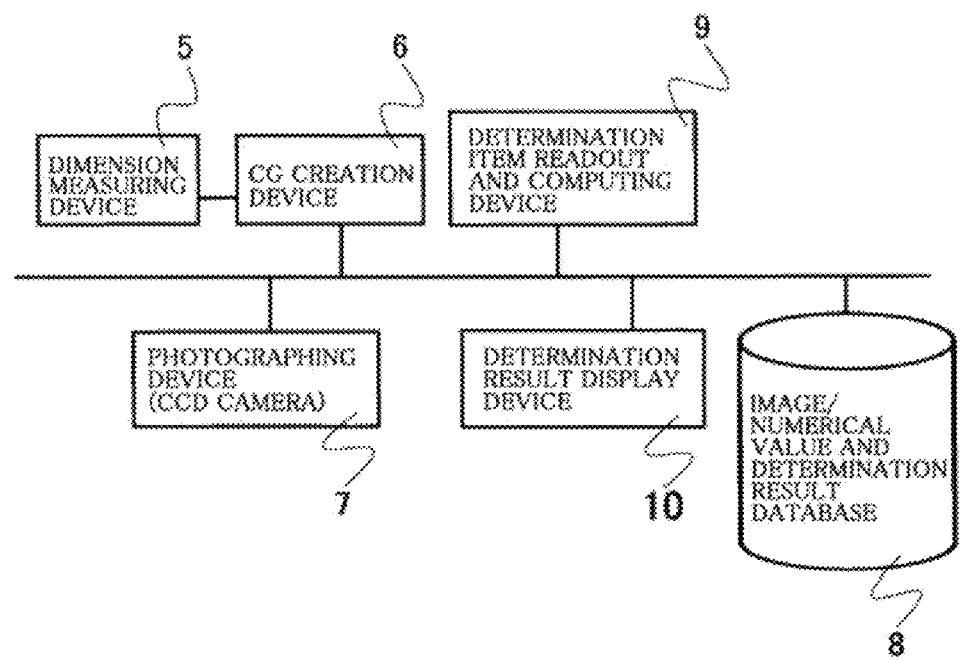
FIG. 17 is an explanatory diagram illustrating the configuration of a device for determining the quality of Heart & Cupid optical effects of a diamond according to the present invention.

FIG. 17 is an explanatory diagram illustrating a device for determining the quality of Heart & Cupid optical effects of the diamond according to the present invention.

There are two means for acquiring Heart & Cupid images. In one means, a diamond 1 with an ID, which is to be determined, is directly imaged by using a photographing device by CCD camera 7. In the other means, data obtained by measuring the diamond 1 with the ID by using a dimension measuring device 5 is read out by computer graphics (CG) to obtain Heart & Cupid images from the pattern of the emitted light. The Heart & Cupid images obtained by photographing or CG are stored in an image/numerical value and determination result database 8 of a computer together with the same ID as the diamond 1 to be determined. A determination result display device 10 determines each of the determination items in rank A (approval), rank C (disapproval), or rank B (sorted into approval or disapproval according to the number of bars) on the basis of each Heart & Cupid image managed by ID via a computing device 9 which has previously read out the numerical value.

Figure 18:
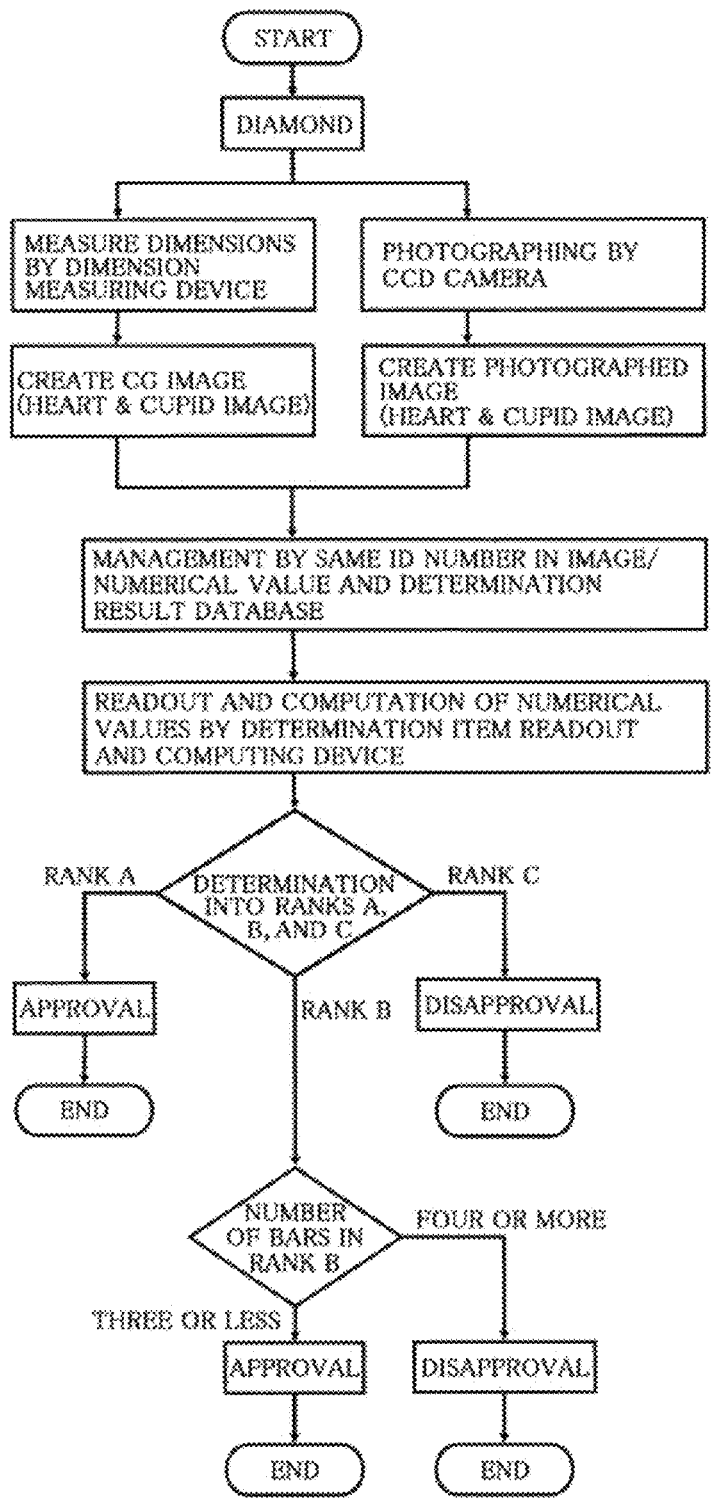
FIG. 18 is a flowsheet illustrating a method of determining the quality of Heart & Cupid optical effects of a diamond according to the present invention.

FIG. 18 is a flowsheet illustrating a method of determining the quality of Heart & Cupid optical effects of the diamond according to the present invention. The Heart & Cupid images are applied to both of the CG image and the photographed image. The numerical values are read out from each of the Heart & Cupid images and computed via the computing device 9. The determination of rank A, rank B, or rank C is performed: rank A is approval; rank C is disapproval; and rank B is approval or disapproval depending on the number of bars.

The present invention enables the quality of a diamond to be determined quantitatively, qualitatively, and objectively in the gem industry, by which the evaluation of the quality becomes uniform, thereby providing the business connections in the industry and consumers with safe transactions and thus further increasing the reliability of the business world.

DESCRIPTION OF REFERENCE NUMERALS

1 Diamond (Round brilliant cut diamond)
2 Heart mark
3 V-shaped mark
4 Cupid mark
5 Dimension measuring device
6 CG creation device
7 Photographing device by CCD camera
8 Image/numerical value and determination result database 8
9 Determination item readout and computing device
10 Determination result display device

The invention claimed is:

1. A method of determining the quality of Heart & Cupid optical effects of a diamond, including the steps of: reading out dimensions, which have been obtained by measuring a round brilliant cut diamond with an ID appended using a dimension measuring device, by computer graphics and outputting Heart & Cupid images and the ID or outputting Heart & Cupid images of the diamond taken by a CCD camera and an ID; storing symmetry data of eight heart marks, namely variation in area of a heart, displacement of a tip portion of each of a heart, the depth of a slit of each heart, a ratio of right and left shoulder widths relative to overall width of each heart, a ratio of a distance in a boundary portion between each heart and a V-shaped mark located on an inner side on a radial line of the heart relative to the overall width of the corresponding heart, a ratio between area of the V-shaped mark and area of a standard heart, and a ratio between right-side length of the V-shaped mark and left-side length of the V-shaped mark, into a computer database; determining ranking of quality of the eight heart marks by performing arithmetic processing of the symmetry data of eight heart marks; and storing said symmetry data of eight cupid marks, namely, a variation in degree obtained from a ratio between a maximum value and a minimum value of each cupid area, whether a straight line connecting an outer tip portion, an intermediate intersection, and a center-side tip of each cupid overlaps another straight line or has a displacement with an angle, and whether an arrow tip portion of each cupid sharply abuts against a girdle or abuts against a girdle portion with a width, into a computer database and determining ranking of quality of the symmetry data of the eight cupid marks by performing arithmetic processing of the symmetry data of eight cupid marks and determining quality ranking by converting into numbers the symmetry data of each heart mark and each cupid mark, by a computer, and performing determination processing by using said computer, wherein ranking determination includes three determined areas where an approved area, a disapproved area, and approved and disapproved areas are present or two determined areas where an approved area and a disapproved area are present.

2. The method of determining the quality of Heart & Cupid optical effects of the diamond in which the diamond is imaged by a CCD camera according to claim 1 includes the step of determining quality by reading out a number of contrasts of said eight heart mark images and said eight cupid mark images using the computer and performing determination processing using the computer.

* * * * *